United States Patent
Cziria et al.

(10) Patent No.: US 12,274,575 B2
(45) Date of Patent: Apr. 15, 2025

(54) ARTIFICIAL INTELLIGENCE-BASED DUAL ENERGY X-RAY IMAGE MOTION CORRECTION TRAINING METHOD AND SYSTEM

(71) Applicant: GE Precision Healthcare LLC, Wauwatosa, WI (US)

(72) Inventors: Balázs P. Cziria, Budapest (HU); German Guillermo Vera Gonzalez, Menomonee Falls, WI (US); Tao Tan, Eindhoven (NL); Pál Tegzes, Budapest (HU); Justin M. Wanek, Madison, WI (US); Gopal B. Avinash, Concord, CA (US); Zita Herczeg, Szeged (HU); Ravi Soni, Livermore, CA (US); Gireesha Chinthamani Rao, Pewaukee, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 315 days.

(21) Appl. No.: 17/965,228

(22) Filed: Oct. 13, 2022

(65) Prior Publication Data
US 2024/0122566 A1    Apr. 18, 2024

(51) Int. Cl.
*A61B 6/00* (2024.01)
*A61B 6/46* (2024.01)
(Continued)

(52) U.S. Cl.
CPC ............ *A61B 6/5264* (2013.01); *A61B 6/463* (2013.01); *A61B 6/467* (2013.01); *A61B 6/482* (2013.01);
(Continued)

(58) Field of Classification Search
CPC ......... A61B 6/463; A61B 6/467; A61B 6/482; A61B 6/5264; G01N 2223/401;
(Continued)

(56) References Cited

U.S. PATENT DOCUMENTS

| 4,872,188 A | 10/1989 | Lauro et al. |
|---|---|---|
| 6,683,934 B1 | 1/2004 | Zhao et al. |

(Continued)

FOREIGN PATENT DOCUMENTS

EP    3034000 A1    6/2016

OTHER PUBLICATIONS

Haskins, G., Kruger, U., &; Yan, P., Deep Learning in Medical Image Registration: A Survey., 2020, pp. 1-30, vol. 31, US.

(Continued)

*Primary Examiner* — Dani Fox
(74) *Attorney, Agent, or Firm* — Boyle Frederickson S.C.

(57) ABSTRACT

A dual energy x-ray imaging system and method of operation includes an artificial intelligence-based motion correction system to minimize the effects of motion artifacts in images produced by the imaging system. The motion correction system is trained to apply simulated motion to various objects of interest within the LE and HE projections in the training dataset to improve registration of the LE and HE projections. The motion correction system is also trained to enhance the correction of small motion artifacts using noise attenuation and subtraction image-based edge detection on the training dataset images reduce noise from the LE projection, consequently improving small motion artifact correction. The motion correction system additionally employs separate motion corrections for soft and bone tissue in forming subtraction soft tissue and bone tissue images, and includes a motion alarm to indicate when motion between LE and HE projections requires a retake of the projections.

20 Claims, 11 Drawing Sheets

(51) Int. Cl.
*G01N 23/04* (2018.01)
*G06T 5/50* (2006.01)
*G06T 5/73* (2024.01)
*G16H 30/40* (2018.01)

(52) U.S. Cl.
CPC .............. *G01N 23/04* (2013.01); *G06T 5/50* (2013.01); *G06T 5/73* (2024.01); *G16H 30/40* (2018.01); *G01N 2223/401* (2013.01); *G06T 2207/10116* (2013.01); *G06T 2207/20081* (2013.01); *G06T 2207/20201* (2013.01); *G06T 2207/20224* (2013.01); *G06T 2207/30004* (2013.01)

(58) Field of Classification Search
CPC .......... G01N 23/04; G06T 2207/10016; G06T 2207/10116; G06T 2207/10144; G06T 2207/20081; G06T 2207/20182; G06T 2207/20201; G06T 2207/20224; G06T 2207/30004; G06T 2207/30008; G06T 2207/30084; G06T 5/50; G06T 5/70; G06T 5/73; G06T 7/33
See application file for complete search history.

(56) References Cited

U.S. PATENT DOCUMENTS

| | | |
|---|---|---|
| 7,961,925 B2 | 6/2011 | Chen et al. |
| 8,180,124 B2 | 5/2012 | Dhanantwari et al. |
| 8,842,936 B2 | 9/2014 | Kawamura |
| 11,284,849 B2 | 3/2022 | Wilson et al. |
| 2003/0215120 A1* | 11/2003 | Uppaluri ............... A61B 6/505 |
| | | 382/128 |
| 2008/0240357 A1 | 10/2008 | Jabri et al. |

OTHER PUBLICATIONS

G. Balakrishnan, A. Zhao, M. R. Sabuncu, J. Guttag and A. V. Dalca, VoxelMorph: A Learning Framework for Deformable Medical Image Registration, Aug. 2019, pp. 1788-1800, vol. 38, No. 8, US.
EP application 23200664.3 filed Sep. 28, 2023—Search Report issued Mar. 6, 2024; 12 pages.
Windsor Rhydian et al: "Self-supervised Multi-modal Alignment for Whole Body Medical Imaging", Sep. 21, 2021 (Sep. 21, 2021), Topics in Cryptology—CT-RSA 2020: The Cryptographers' Track at the RSA Conference 2020, San Francisco, CA, USA, Feb. 24-28, 2020, Springer, 201 Olin Library Cornell University Ithaca, NY 14853, pp. 90-101, XP047611219 [retrieved on Sep. 21, 2021].

* cited by examiner

Rib motion artifact compensation

Airways/lung tissue artifact compensation

Rib motion artifact compensation

Airways/lung tissue artifact compensation

ARTIFICIAL INTELLIGENCE-BASED DUAL ENERGY X-RAY IMAGE MOTION CORRECTION TRAINING METHOD AND SYSTEM

FIELD OF THE DISCLOSURE

This disclosure relates generally to motion correction methods and systems for x-ray images and methods of training artificial intelligence modules to be employed as part of the motion correction system.

BACKGROUND OF THE DISCLOSURE

In dual energy x-ray imaging techniques, a subject to be imaged is exposed x-rays having different energies by a dual energy x-ray system in order to produce x-ray images of different types of tissue and/or structures disposed within the subject being imaged. The tissues and/or structures located within the subject have varying x-ray attenuations, such that x-rays of different energies will be absorbed differently by different types of tissue and/or structures.

When used to obtain images of a mammalian subject, e.g., a human, the differences in the absorption of the low energy x-rays and the high energy x-ray images by the various tissues of the subject, e.g., more dense or hard tissues, i.e., bone, and less dense or soft tissues, i.e., internal organs, enable the dual energy x-ray system to produce images that primarily illustrate tissues of one type or the other. This separation or decomposition of the anatomy of the patient being scanned enables each type of tissue to be presented in a separate image, the soft tissue image or the bone image, where one type of tissue is illustrated in a manner to more clearly illustrated the tissue with the other type being removed to prevent obscuring of the structures of the desired tissue by structures of the undesired tissue.

While capable of providing images that enable more clear visualization and diagnosis of different types of tissue, the dual energy imaging system and process does present certain issues. In particular, when dual energy images are obtained, such as when utilizing a single x-ray source or fast-switching dual energy imaging systems, as a result of obtaining consecutive images of the patient there is often movement in the position of the patient. This movement of the patient results in the low energy image and the high energy image not being obtained on the subject in the same position, i.e., the low energy image and the high energy image are misaligned.

In order to correct for this motion, or align the low energy image with the high energy image, a variety of motion correction processes can be employed. A number of these motion correction processes can be performed by artificial intelligence employed on the imaging system. To enable the artificial intelligence to properly correct for motion between the low and high energy images, the artificial intelligence must first be trained to perform this task.

However, there are certain shortcomings in the training processes currently employed for an artificial intelligence-based motion correction system. For example, in the situation where the artificial intelligence is being trained to detect and correct for motion in one or more portions of the subject, e.g., movement of ribs, an organ, such as the heart, and/or other structures, such as the diaphragm, within the subject, being imaged, prior unsupervised training processes do not adequately compensate for the movement of such structures between the low and high energy images in order to register the images/image data with one another for decomposition purposes.

Further, current training procedures for artificial intelligence-based motion correction system or modules have the ability to correct for large motion artifacts but do not adequately correct for small motion artifacts and for contradictory motion areas that are difficult to manually discern and correct. In significant part, the difficulty with correction of the smaller motion artifacts is created due to the increased noise present in the low energy image and its effect on the determination of the location of soft tissues within the low energy image.

In addition, concerning the implementation of the artificial intelligence-based motion correction system in an x-ray imaging system, current motion correction systems employ a single motion correction to each of the low energy image data and the high energy image data prior to decomposition or subtraction to from the low energy image and the high energy image. However, because certain features are desired to be represented more clearly in a particular image, i.e., the soft tissue in a low energy image and the bone in a high energy image, it may be preferred that separate motion correction applied to correct for motion of each type of tissue respectively.

Finally, also with regard to the implementation of the artificial intelligence-based motion correction system on the dual energy x-ray imaging system, current motion correction systems provide motion correction for larger tissue movements. However, the motion correction systems do not adequately assess the magnitude of the movement that occurred between the low energy image and the high energy image in order to determine if the amount of movement is significant enough to create significant artifacts in the resulting images. As a result, it is not until the low energy image and the high energy image are reviewed that the significance of the artifacts and the negative effects on the diagnosis can be determined.

Thus, it us desirable to develop a training process for an artificial intelligence-based motion correction system employed within a dual energy imaging system which can train the motion correction system to more accurately correction for the movement of organs and associated structures within the imaged subject to provide better registration between the low energy image and the high energy image. It is also desirable to develop a training procedure for the motion correction system that provides better motion correction for smaller motion artifacts within noisy images. Finally, it is also desirable to develop an improved implementation of the artificial intelligence-based motion correction system within a dual energy imaging system by providing separated motion corrections for soft tissue generation and dense or bone tissue generation, as well as to provide a motion alarm when an excessive amount of movement is detected between the low energy image and the high energy image.

SUMMARY OF THE DISCLOSURE

According to one aspect of an exemplary embodiment of the disclosure, a method for improving motion correction in images of a subject obtained from a dual energy subtraction radiography x-ray system includes the steps of providing an x-ray system having an x-ray source, and an x-ray detector alignable with the x-ray source, an image processing system operably connected to the x-ray source and x-ray detector to operate the x-ray source to generate HE and LE x-ray image data, the image processing system including a processing unit for processing the HE and LE x-ray image data from the detector to form an actual HE image and an actual LE image from the image data, non-transitory memory operably connected to the processing unit and storing instructions for the operation of a motion correction system, a display operably connected to the image processing system for presenting the images to a user and a user interface operably connected to the image processing system to enable user input to the image processing system, operating the x-ray system to obtain the HE and LE x-ray image data, forming the actual HE x-ray image and the actual LE x-ray image and performing a first subtraction process on the actual HE x-ray image and the actual LE x-ray image to form at least one of a soft tissue image and a bone tissue image after employing the motion correction system to apply the first motion correction to the actual HE x-ray image and the actual LE x-ray image.

According to still another aspect of an exemplary embodiment of the present disclosure, a method for improving motion correction in images of a subject obtained from a dual energy subtraction radiography x-ray system including the steps of providing an image processing system capable of processing image data comprising one or more high energy (HE) x-ray image(s) and one or more low energy (LE) x-ray image(s) of the subject, the image processing system having a processing unit for processing the HE x-ray image data and the LE x-ray image data to form images and non-transitory memory operably connected to the processing unit and storing instructions for the operation of a motion correction system employed within the image processing system, providing a training dataset including a number of pairs of training HE x-ray images and training LE x-ray images of one or more objects, training the motion correction system to register one of the training HE x-ray image and the training LE x-ray image of each training dataset pair to the other of the training HE x-ray image and the training LE x-ray image of each training dataset pair by applying a first motion correction to the training x-ray image pair, and employing the motion correction system on a dual energy x-ray imaging system to apply the first motion correction to an actual HE image and an actual LE image obtained by the dual energy x-ray imaging system.

According to still another aspect of an exemplary embodiment of the disclosure, a dual energy x-ray system includes an x-ray source, and an x-ray detector alignable with the x-ray source, an image processing system operably connected to the x-ray source and x-ray detector to generate x-ray image data, the image processing system including a processing unit for processing the x-ray image data from the detector, non-transitory memory operably connected to the processing unit and storing instructions for operation of a motion correction system, a display operably connected to the image processing system for presenting information to a user, and a user interface operably connected to the image processing system to enable user input to the image processing system wherein the processing unit and non-transitory memory for the motion correction system is configured to apply a first motion correction to HE and LE x-ray images to facilitate the computation of soft tissue subtraction, and to apply a second motion correction to the HE and LE x-ray images to facilitate the computation of bone tissue subtraction.

According to still another aspect of an exemplary embodiment of the disclosure, an x-ray system includes an x-ray source, and an x-ray detector alignable with the x-ray source, an image processing system operably connected to the x-ray source and x-ray detector to operate the x-ray source to generate HE and LE x-ray image data, the image processing system including a processing unit for processing the HE and LE x-ray image data from the detector to form an actual HE image and an actual LE image from the image data, non-transitory memory operably connected to the processing unit and storing instructions for the operation of a motion correction system, a display operably connected to the image processing system for presenting the images to a user and a user interface operably connected to the image processing system to enable user input to the image processing system, wherein the processing unit and non-transitory memory for the motion correction system is configured to obtain the actual HE x-ray image and the actual LE x-ray image of the subject and to register the actual HE x-ray image to the actual LE x-ray image by applying a first motion correction to the actual HE x-ray image and the actual LE x-ray image via the motion correction system.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings.

DETAILED DESCRIPTION OF THE DRAWINGS

Figure 1:
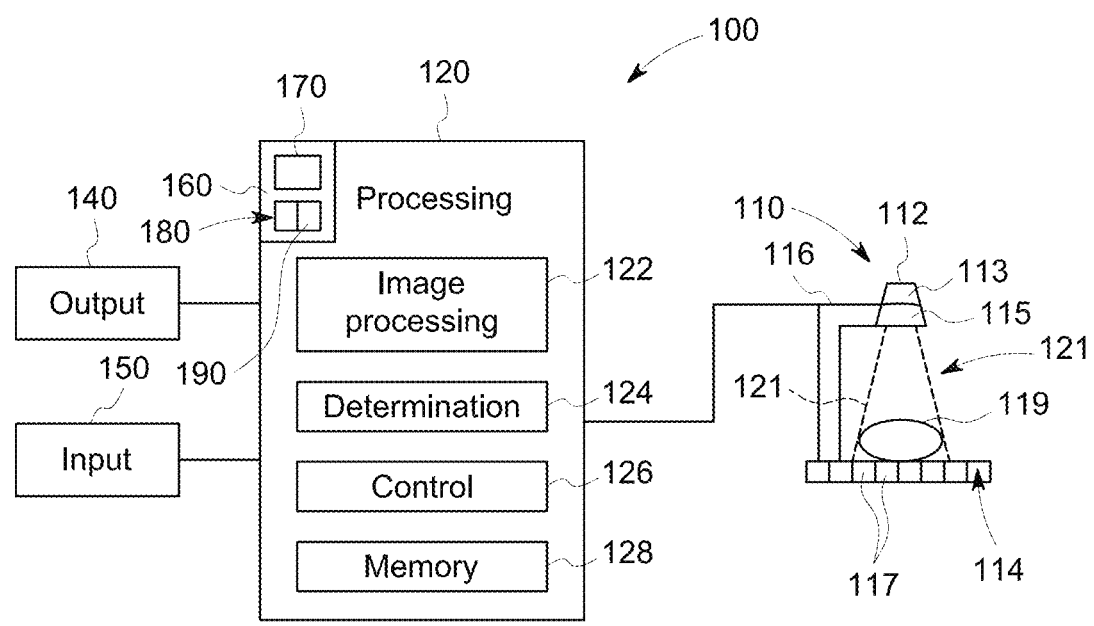
FIG. 1 is a block schematic diagram of an exemplary imaging system according to an exemplary embodiment of the disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for improving performance of X-ray systems using multiple voltages or energies, such as dual-energy spectral imaging systems utilizing an X-ray source that operates at a high voltage and a low voltage. Various embodiments improve and/or optimize or improve a motion artifact reduction in low and high energy images to provide improved imaging performance. Various embodiments provide improved imaging. A technical effect of at least one embodiment includes improved motion artifact reduction for dual-energy imaging.

Referring to FIG. 1, an exemplary embodiment of the system 10, such as that disclosed in U.S. Pat. No. 6,683,934 entitled Dual Energy X-Ray Imaging System And Method For Radiography And Mammography, the entirety of which is hereby expressly incorporated by reference for all purposes, may be utilized to obtain x-ray images or projections of the anatomy and/or an object disposed within or as part of the anatomy of a patient.

FIG. 1 illustrates an dual energy imaging system 100 in accordance with an embodiment. The imaging system 100 may be configured, for example, to perform x-ray scanning of an object, such as a human or animal patient (or portion thereof). The imaging system 100 includes an acquisition unit 110 and a processing unit 120. Generally, the acquisition unit 110 is configured to acquire projection data or imaging data, while the processing unit 120 is configured to control the operation of the acquisition unit 110, and to reconstruct images using the data acquired by the acquisition unit 110. It may be noted that various embodiments may include additional components, or may not include all of the components shown in FIG. 1 (for example, various embodiments may provide sub-systems for use with other sub-systems to provide an imaging system). Further, it may be noted that certain aspects of the imaging system 100 shown as separate blocks in FIG. 1 may be incorporated into a single physical entity, and/or aspects shown as a single block in FIG. 1 may be shared or divided among two or more physical entities.

The depicted acquisition unit 110 includes an X-ray source 112 and a detector 114. The depicted X-ray source 112 includes a generator 113 and a tube 115. The generator 113 may be used to control (e.g., via input signals from the processing unit 120) the supply of power to the tube 115 to change the energy level or voltage level of the tube 115. For example, the X-ray source 112 may be utilized to provide varying energy levels during the course of operation. In some embodiments, the X-ray source 112 may be configured to be switched between a high voltage (e.g., a nominal 140 kV) and a low voltage (e.g., a nominal 80 kV) as the acquisition unit 110 obtains image data of an object. In some embodiments, the voltage may be switched from view to view (e.g., a given view at the high voltage or energy level, the immediately subsequent view at the low voltage or energy level, the next immediately subsequent view at the high voltage or energy level, and so forth).

Generally, X-rays from the X-ray source 112 may be guided to an object to be imaged through a source collimator and bowtie filter. The object to be imaged, for example, may be a human patient, or a portion thereof (e.g., head or torso, among others). The source collimator may be configured to allow X-rays within a desired field of view (FOV) to pass through to the object to be imaged while blocking other X-rays. The bowtie filter module may be configured to absorb radiation from the X-ray source 112 to control distribution of X-rays passed to the object to be imaged.

X-rays that pass through the object to be imaged are attenuated by the object and received by the detector 114 (which may have a detector collimator associated therewith), which detects the attenuated X-rays and provides imaging information to the processing unit 120. The depicted detector array 114 includes a plurality of detector elements 117. Each detector element 117 produces an electrical signal, or output, that represents the intensity of an impinging X-ray beam and hence allows estimation of the attenuation of the beam as it passes through the subject 119. FIG. 1 shows only a single row of detector elements 117 (i.e., a detector row). However, the multislice detector 114 includes a plurality of parallel detector rows of detector elements 117 such that projection data corresponding to a plurality of slices can be acquired simultaneously during a scan.

The processing unit 120 may then reconstruct an image of the scanned portion of the object using the imaging data information provided by the detector 114/detector elements 117. The processing unit 120 may include or be operably coupled to the output unit 140, which in the illustrated embodiment is configured to display an image, for example, an image created by the processing unit 120 using imaging information from the detector 114. The depicted input unit 150 is configured to obtain input corresponding to a scan to be performed, with the processing unit 120 using the input to determine one or more scan settings (e.g., tube voltage, tube current, scanning rotation speed, or the like). The input unit 150 may include a keyboard, mouse, touchscreen or the like to receive input from an operator, and/or may include a port or other connectivity device to receive input from a computer or other source.

As indicated herein, the processing unit 120 is configured to control various aspects of the acquisition unit 110 and/or to create an image using information obtained via the acquisition unit 110. For example, the processing unit 120 may be configured to create an image using information collected by the acquisition unit 110.

The depicted processing unit 120 is operably coupled to the input unit 150, the output unit 140, and the acquisition unit 110. The processing unit 120, for example, may receive information regarding a scan from the input unit 150 that may be utilized in determining a desired clinical task, patient information, and/or scanning parameters to be used for a given imaging scan to be performed with the imaging system 100. As another example, the processing unit 120 may receive imaging data or projection data from the detector 114. As one more example, the processing unit 120 may provide control signals to one or more aspects of the acquisition unit 110, such as the X-ray source 112 and detector 114. The processing unit 120 may include processing circuitry configured to perform one or more tasks, functions, or steps discussed herein. It may be noted that "processing unit" as used herein is not intended to necessarily be limited to a single processor or computer. For example, the processing unit 120 may include multiple processors and/or computers, which may be integrated in a common housing or unit, or which may distributed among various units or housings.

The depicted processing unit 120 is configured to control the acquisition unit 110 (e.g., by controlling the activation and deactivation of the X-ray source 112, as well as the energy or voltage level of the X-ray source 112), and to collect imaging information during an imaging scan.

Further, the exemplary imaging system 100 may be utilized to implement various embodiments discussed herein. Although the imaging system 100 is illustrated as a standalone imaging system, it should be noted that the imaging system 100 may form part of a multi-modality imaging system in some embodiments. For example, the multi-modality imaging system may include the imaging system 100 and a positron emission tomography (PET) imaging system, or a single photon emission computed tomography (SPECT) imaging system. It should also be understood that other imaging systems capable of performing the functions described herein are contemplated as being used.

In the illustrated embodiment, the processing unit 120 includes a image processing module 122, a determination module 124, a control module 126, and a memory 128. It may be noted that other types, numbers, or combinations of modules may be employed in alternate embodiments, and/or various aspects of modules described herein may be utilized in connection with different modules additionally or alternatively. Generally, the various aspects of the processing unit 120 act individually or cooperatively with other aspects to perform one or more aspects of the methods, steps, or processes discussed herein. It may be noted that the memory 128 may include one or more databases, lookup tables, or other sources of stored information utilized by the processing unit 120 to perform the required functions. It may further be noted that the memory 128 may have stored thereon instructions for directing the processing unit 120 to perform one or more aspects of the methods, steps, or processes discussed herein.

The depicted image processing module 122 is configured to create one or more images using imaging or projection data acquired from the detector 114. For example, the image processing module 122 may receive imaging information from the detector 114 taken over a number of views (e.g., for a number of projection taken at different positions along the length of an object to be imaged) and create an image used for diagnostic purposes. The created images are stored in memory 128 or in any other suitable storage medium or device operably connected to the image processing module 122.

In the illustrated embodiment, the determination module 124 is configured to determine one or more motion corrections to be applied to the projections and/or images provide to and by the image processing module 122. In some embodiments, the determination module 124 may access a database and/or lookup table stored on the memory 128 that includes instructions for the operation of the determination module 124 to perform the desired motion correction processes on the projection and/or image data, such as dual energy projection and/or image data that is utilized to form dual energy images and to register those images with one another prior to undergoing a subtraction process to form subtracted soft tissue and bone images.

In various embodiments, the determination module 124 may be communicably coupled to the control module 126, with the control module 126 configured to control the acquisition unit 110 and/or other aspects of the system 100 to perform the imaging scans using one or more waveform configurations for the acquisition unit 110 called for by the determination module 124. For example, the X-ray source 112 may be controlled to switch between a high energy level and a low energy level over a fall time and duty cycle specified by the determination module 124, and may utilize a voltage threshold specified by the determination module to bin acquired data.

The output unit 140 is configured to provide information to the user. The output unit 140 may be configured to display, for example, a reconstructed image or, as another example, may display a selected or determined motion overlay on a displayed dual energy image for a displacement field determined by the determination module for approval by an operator or technician. The output unit 140 may include one or more of a screen, a touchscreen, a printer, or the like.

The input unit 150 may be configured to obtain an input that corresponds to one or more settings or characteristics of a scan to be performed, and to provide the input (or information corresponding to the input) to the processing unit 120, which may use the input to determine the associated motion correction. The input may include, for example, a clinical task (e.g., diagnose kidney stones) and/or portion of the body to be scanned (e.g., head, body). The input unit 150 may be configured to accept a manual user input, such as via a touchscreen, keyboard, mouse, or the like. Additionally or alternatively, the input unit 150 may receive information from another aspect of the imaging system 100, another system, or a remote computer, for example, via a port or other connectivity device. The input unit 150 may also be configured to obtain user approval or denial of a proposed scanning setting.

The imaging system 100 can also includes a computer 160 forming part of or encompassing the processing unit 120 that receives the projection data from the detector array 114 and processes the projection data to reconstruct an image of the subject. The computer 160, for example, may include one or more aspects of the processing unit 120, such as the image processing module 122 and/or the determination module 124, and/or can be operably coupled to one or more aspects of the processing unit 120.

In various embodiments, the computer 160 includes a device 170, for example, a CD-ROM drive, DVD drive, magnetic optical disk (MOD) device, or any other digital device including a network connecting device such as an Ethernet device for reading instructions and/or data from a tangible non-transitory computer-readable medium or memory 128, that includes signals, such as a CD-ROM, a DVD or another digital source such as a network or the Internet, as well as yet to be developed digital means. In another embodiment, the computer 160 executes instructions stored in firmware (not shown). The computer 160 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 112 and the detector array 114 positioned by the gantry 116 within the imaging plane around the subject 119 to be imaged such that an X-ray beam 121 intersects the subject 119. In a scan, the projection data from the detector 114 is processed to create an image that corresponds to a two-dimensional image taken of the subject 119.

Figure 2:
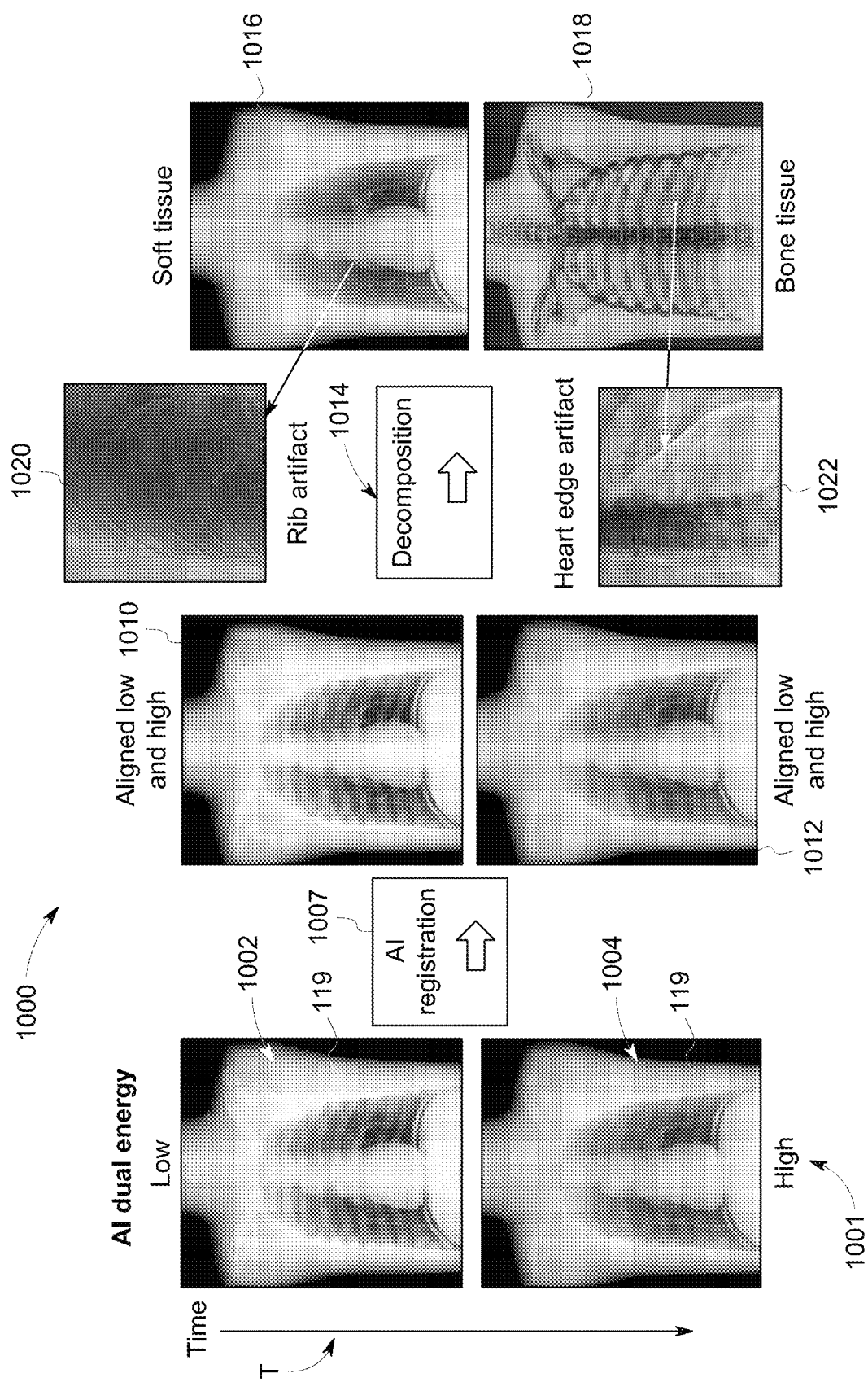
FIG. 2 is a schematic diagram of an exemplary method generation of subtracted soft tissue and bone images from LE and HE projections obtained by a dual energy imaging system.

Looking now at FIG. 2, an exemplary dual energy imaging process 1000 is illustrated which can be performed utilizing the system 100 of FIG. 1. In the process 1000, the processing unit 120 includes an AI-based motion correction system 180, which can be formed with or at least in part of a machine learning model, and/or a deep learning (DL) model 190, such as those disclosed in U.S. Pat. No. 11,003,988, entitled Hardware System Design Improvement Using Deep Learning Algorithms, the entirety of which is hereby expressly incorporated by reference for all purposes, where the AI-based motion correction system 180 and/or DL model 190 are trained to provide motion correction to low energy (LE) and high energy (HE) projections obtained by the system in order to improve the registration of the LE and HE projections to produce LE and HE images. The system including a deep learning (DL) model of the system 100 is operated in a first step 1001 to obtain a low energy projection/image data 1002 and a high energy projection/image data 1004 of the subject 119. The low energy projection/image data 1002 is obtained prior in time T to the high energy projection/image data 1004, such that movement of one or more of the structures of the subject 119 being imaged occurs. As a result of this movement, when the low energy projection 1002 is registered to and/or aligned with the high energy projection 1004 in a subsequent step 1007 by the processing unit 120/computer 160 to form at least one of an aligned low energy image 1010 and/or an aligned high energy image 1012, the registration process must accommodate for the movement between the structures in the time between the low energy projection 1002 and the high energy projection 1004. If not sufficiently addressed in the registration step 1007, when the aligned low energy image 1010 and aligned high energy image 1012 are run through a decomposition step 1014 where the respective images 1010 and 1012 are subjected to processing to remove image data relating to specified types of tissues, i.e., removal of dense or bone tissue in the aligned low energy image 1010 and removal of soft tissue in the aligned high energy image 1012, the soft tissue image 1016 and dense or bone tissue image 1018 output from the decomposition process can include significant artifacts 1020,1022 present due to the insufficient motion correction in producing and/or post-processing of the aligned images 1010,1012.

To improve the motion correction between the aligned low energy image 1010 and the aligned high energy image 1012, according to one exemplary embodiment of the present disclosure, the AI-based motion correction system 180/DL model 190, and in particular the registration function G of the AI-based motion correction system 180/DL model 190 is trained and/or optimized to better accommodate for organ motion artifacts present within the low energy projection 1002 and/or the high energy projection 1004, In various embodiments, the training can be performed directly on the imaging system 100, or on a separate computing system (not shown) where the AI-based motion correction system 180/DL model 190 is transferred to the imaging system 100 after training. When training the registration function G of the AI-based motion correction system 180/DL model 190, the AI-based motion correction system 180/DL model 190 training may utilize a simulated motion to structures such as bones and organs present within and undergo motion between the low energy projection 1002 and/or the high energy projection 1004 and in a supervised manner optimize the prediction to be the simulated motion using a loss function between the predicted and simulated motions.

Figure 3:
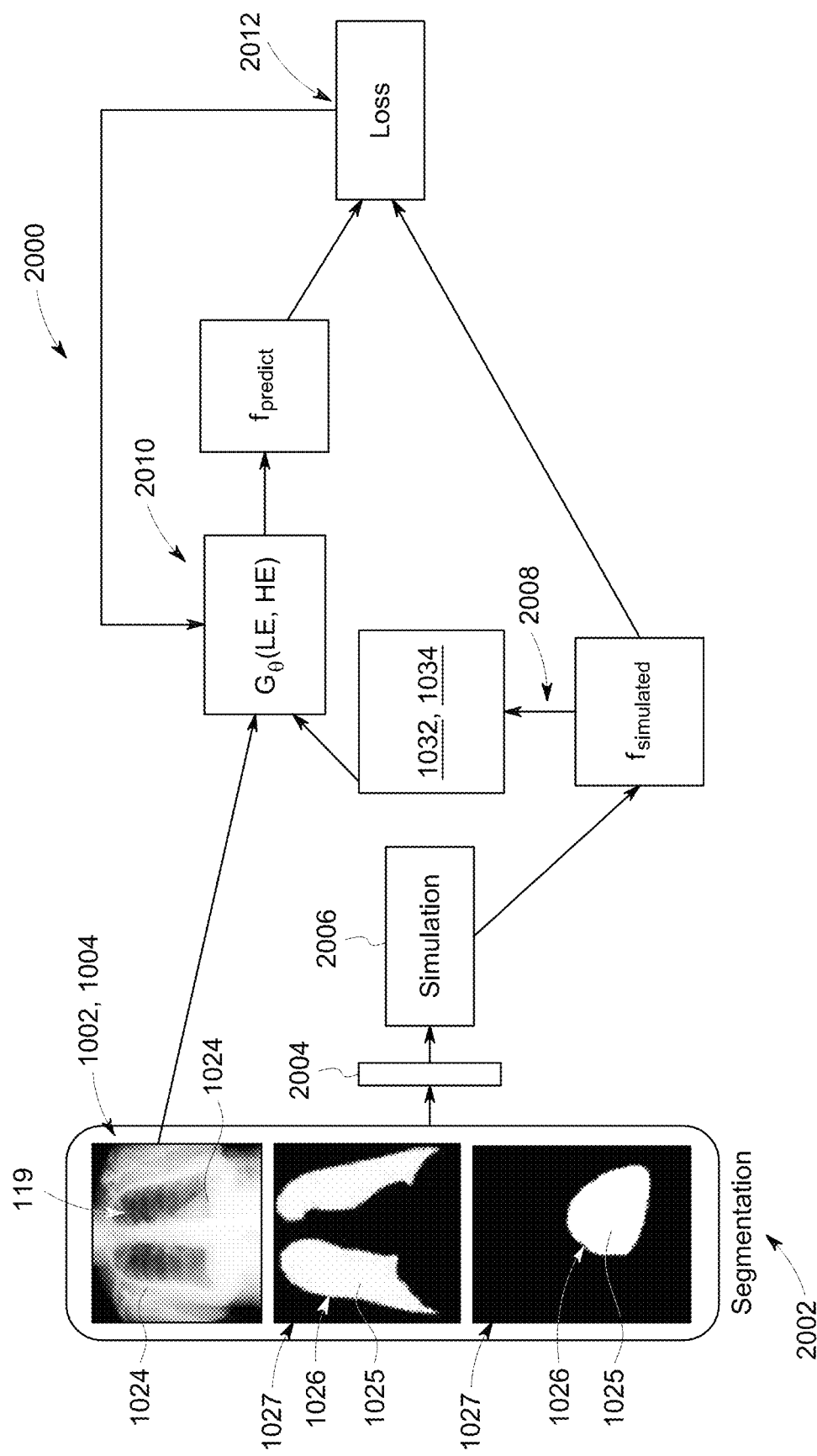
FIG. 3 is a schematic view of a supervised training method for an artificial intelligence-based motion correction system for a dual energy imaging system according to an exemplary embodiment of the disclosure.

Referring now to FIG. 3, in a first step 2002 of the supervised simulated motion training process 2000, the AI-based motion correction system 180/DL model 190 segments one or more objects of interest 1024 illustrated within a pair of associated images form a training dataset containing multiple pairs of associated images, i.e., a low energy projection 1002 and a high energy projection 1004, in order to determine the border 1026 of the object(s) of interest 1024 within the projections 1002,1004. The object(s) of interest 1024 is/are portions of the imaged subject 119 that undergo motion between the low energy projection 1002 and the high energy projection 1004. The object(s) of interest 1024 can be defined manually and/or automatically, and can be selected to correspond to the focus of imaging process performed by the imaging system 100, such as one or more of the ribs, the heart, and/or the lungs, among others. In a subsequent step 2004, the training procedure selects the low energy projection 1002 or high energy projection 1004 to which simulated movement is to be provided to the object(s) of interest 1024 in the selected low energy projection 1002 or the high energy projection 1004 which are separated from the projections 1002,1004 into segmented images 1027 of the segmented objects of interest 1025. In the following step 2006, a simulated motion field $f_{simulated}$, i.e., movement the object(s) of interest 1024 in the selected projection 1002, 1004, is generated to represent the simulated movement of the object 1024 occurring between the low energy projection 1002 and the high energy projection 1004. To generate the simulated motion field $f_{simulated}$ in step 2006, the training procedure may apply any combination of a) random translations of the segmented objects 1025, b) random motion field, c) utilize the provided segmented objects of interest 1025 to determine a corresponding movement field, via erosion (contraction) and/or dilation (expansion) to be applied the pixels within the segmented object(s) of interest 1025 and determine a motion field around the boundary of the objects or d) other methods. For any regions of the image 1002,1004 that do not contain a portion of the segmented object(s) of interest 1025, the amount of the translation is selected to be zero (0). In addition, in view of differences between the types of objects of interest 1024 contained in the projection 1002,1004, the random translation can be selected to be different (i.e., larger or smaller) for each segmented object of interest 1025 in order to more accurately accommodate for the magnitude of movement to be expected for each type of object of interest 1024. In one particular exemplary embodiment, the simulated anatomical movement is produced by traditional image processing method/module or some generative deep learning method to produce such motions.

Once the simulated motion field $f_{simulated}$ is determined, in step 2008 each simulated motion field $f_{simulated}$ is applied to the associated segmented object of interest 1025 in the segmented images 1027 to generate a simulated fixed image 1032,1034. In step 2010, this simulated fixed image 1032, 1034 is then compared with or registered to the original projection 1002,1004 to which the simulated motion field(s) $f_{simulated}$ was applied using the registration function G for the AI-based motion correction system 180/DL model 190 to generate a predicted motion field $f_{predict}$ for each of the segmented objects of interest 1025 in the projections 1002, 1004 and images 1032,1034.

In step 2012, the training procedure compares the predicted motion field(s) $f_{predict}$ with the simulated motion field(s) $f_{simulated}$ to determine a supervised loss 2014 that is returned to the registration function G to optimize the image registration function G of the AI-based motion correction system 180/DL model 190 in generating the predicted motion field(s) $f_{predict}$.

The registration function G of the AI-based motion correction system 180/DL model 190 is then applied to each of the low energy projection 1002 and the high energy projection 1004 in the training dataset pairs to generate a combined predicted motion field $f_{predict\_low\_high}$ for the low energy projection 1002 and for the high energy projection 1004. The combined predicted motion field $f_{predict\_low\_high}$ is then applied to the segmented object(s) of interest 1025 to form moved masks which are subsequently compared with the corresponding masks of the objects of interest 1024 in the high energy projection 1004 to further optimize the registration function G. Once the registration function G has been sufficiently optimized, the AI-based motion correction system 180/DL model 190 can be transferred onto and/or employed on the imaging system 10 to provide the optimized registration function G between associated pairs of low energy projections 1002 and high energy projections 1004 obtained by the imaging system 100.

The transformation of segmented object(s) of interest 1025 with $f_{predict}$ leads to an additional loss term $L_{seg}$. This is used in the unsupervised loss part. For simulated movement the desired $f_{simulated}$ solution is known, so a supervised loss can be used directly and there is no point to transform the object(s) of interest 1025 to compute $L_{seg}$. For supervised loss part the segmented object(s) of interest 1025 can be used to set up anatomically relevant $f_{simulated}$ motion. Overall, the training can be based on the combination of one or more of the following losses: the supervised $L_{flow}$ loss from FIG. 3, the unsupervised $L_{seg}$ loss from FIG. 4, the unsupervised $L_{sim}$ loss from FIG. 4 and a regularization loss $L_{smooth}$ on motion field from FIG. 4 where it is used in the case of using unsupervised training $L_{sim}$ and $L_{seg}$ losses. Once all the utilized losses are determined, then they are combined into an overall training loss and the G is optimized to minimize this training loss.

Figure 4:
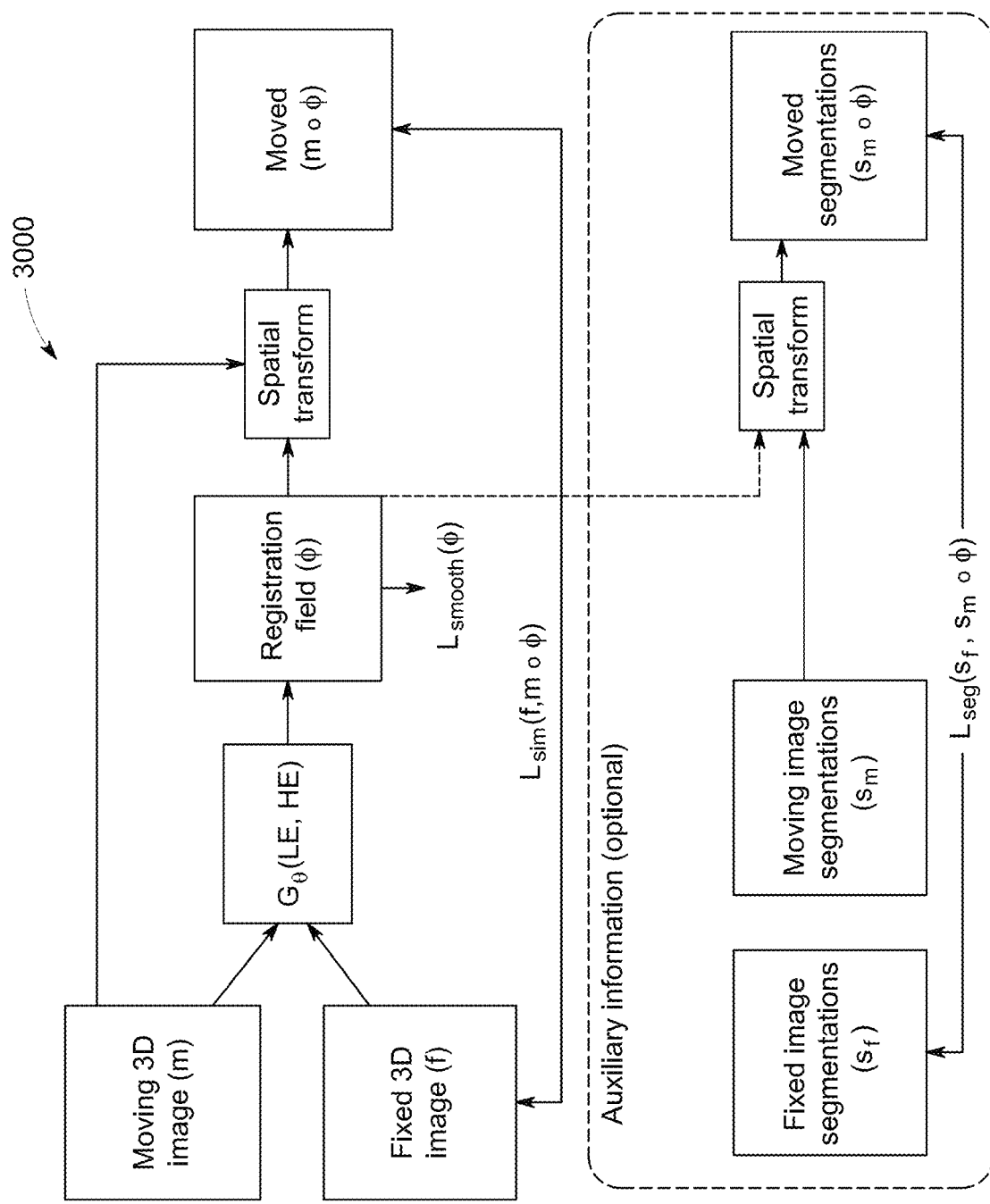
FIG. 4 is a schematic view of an unsupervised training method for an artificial intelligence-based motion correction system for a dual energy imaging system utilized with the supervised method of FIG. 3, according to an exemplary embodiment of the disclosure.

Looking now at FIG. 4, with the function G for AI-based motion correction system 180/DL model 190 optimized utilizing an unsupervised learning/training by specifying an image distance metric to measure the difference between the aligned LE and HE images ($L_{sim}$), utilizing a regularization on the motion correction ($L_{smooth}$) to restrict the correction to more realistic motions and optionally utilizing an image distance metric on the provided structures 1024 that supposed to be aligned after motion correction ($L_{seg}$). The DL model can be trained solely in an unsupervised training method or solely in a supervised training method, or using both supervised and unsupervised training methods at the same time, as the supervised vs unsupervised distinction is just a difference in the way the training samples are constructed and what the optimal solution is specified for that sample.

Figure 5:
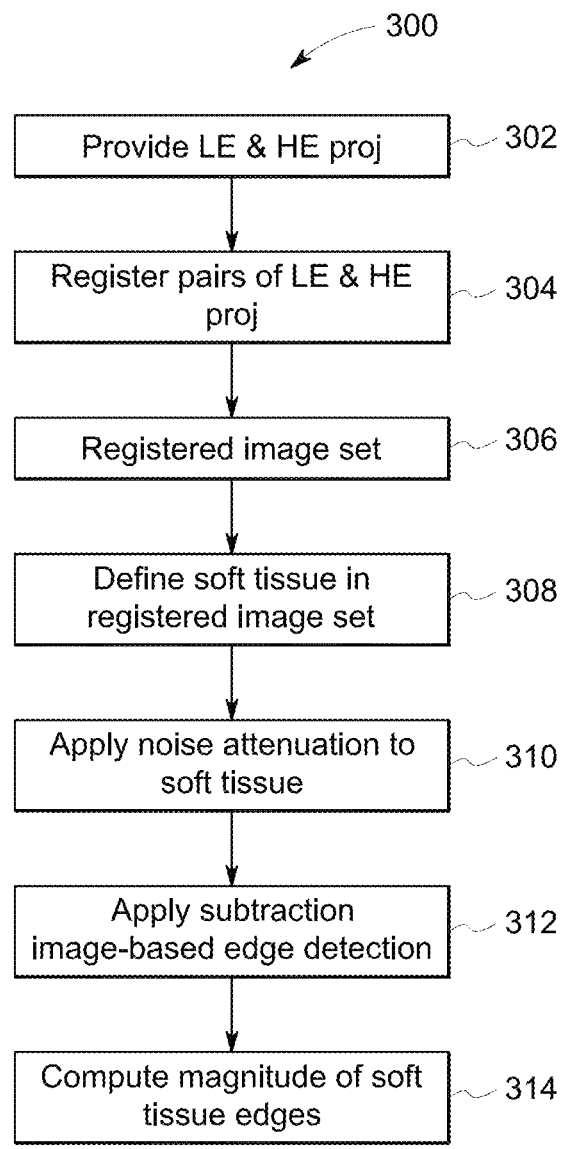
FIG. 5 is a flowchart illustrated a method for the operation of an edge detection and noise attenuation AI-based motion correction system, according to one exemplary embodiment of the disclosure.
Figure 6:
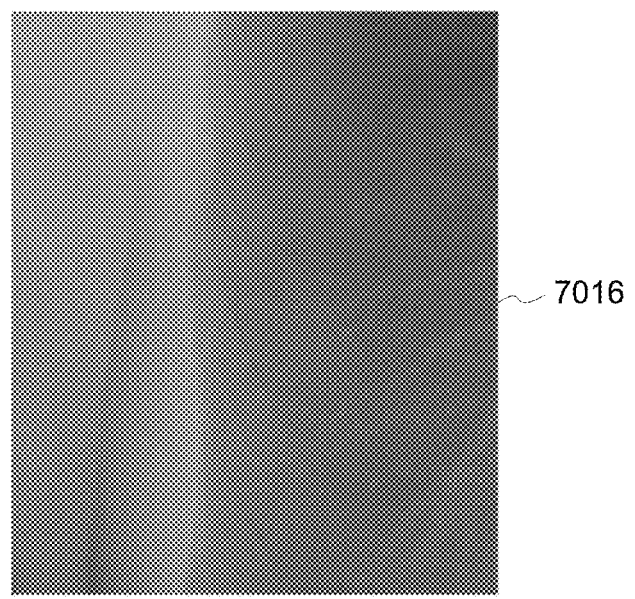
FIG. 6 is an illustration of small uncorrected or introduced motion artifacts along rib edges.

Referring now to FIGS. 5-6, in accordance with another exemplary embodiment of the present disclosure which can be employed along with or separately from the embodiment for the training of the AI-based motion correction system 180/DL model 190 described with regard to FIGS. 2-4, the AI-based motion correction system 180/DL model 190 is trained, either directly in the imaging system 100 or on a separate computing system and transferred onto the imaging system 100 after training, to provide improved motion correction with regard to small motion artifacts and contradictory motion areas. In prior art motion correction systems, deep learning (DL) models are utilized that are trained in unsupervised processes to minimize losses such as cross-correlation (CC), mean squared error (MSE) and locally normalized MSE, in order to correct motion artifacts in x-ray images. However, with these DL models, the losses utilized in the unsupervised training process for these DL models often times are not precise enough to match small motions in dual energy imaging between the low and high energy images and indicate that dual energy specific image distance metric (loss) is needed. While subtraction image based edge detection processes employed particularly with regard to dual energy imaging can enhance the sensitivity of the DL model with regard to motion artifacts, the low energy image 7018 includes a significant amount of noise that can be translated into the subtracted soft tissue image, the direct edge detection processes do not adequately correct for small motion artifacts, particularly with regard to corrections within the soft tissue represented in the subtracted soft tissue image 7018, and can actively introduce artifacts into the subtracted soft tissue image 7018, as shown in FIG. 6.

Therefore, according to an exemplary embodiment of the present disclosure, the AI-based motion correction system 180 including a DL model 190 is trained using an unsupervised loss minimization process similar to that in prior art DL models to correct motion for multi-modality image registration. However, the DL model 190 is trained in combination with a dual energy subtraction image edge metric/noise attenuation. The performance of the loss for unsupervised training is improved over prior art systems by utilizing the soft tissue edge detection based loss component, including the implementation of noise attenuation to minimize noise brought into the subtracted soft tissue image 1016 from the low energy projection 1002 and/or low energy image 1010.

In particular, with reference to FIG. 5, the method 300 of training AI-based motion correction system 180 including the DL model 190 operates to predict a motion correction field within supplied pairs of associated low and high energy images in a training dataset to minimize a loss function based on the determination of the magnitude of the soft tissue edges in the motion correction field. The method 300 is part of the computation of $L_{sim}$ and is operating on a training dataset of unregistered images. During optimization a pair of unregistered images is inputted into registration G to get $f_{predicted}$. Based on $f_{predicted}$ the DL model 190 computes aligned LE and HE as in FIG. 2, as in step 306. From aligned LE and HE images, the training procedure computes soft tissue using a subtraction procedure in step 308. Noise attenuation 310 is used during the subtraction procedure.

In the method 300, in initial step 302 the DL model 190 is provided with a training dataset including a number of pairs of associated low energy projections 1002 and high energy projections 1004 of a subject 119. In step 304, the DL model 190 operates to register the high energy projections 1002 to the low energy projections 1004 in a known manner to output a candidate registered image set 306 of aligned low and high energy images 1010, 1012. The training procedure in step 308 then employs the dual energy subtraction to compute the soft tissue present within the candidate registered image set 306. Subsequent to the noise attenuation, the training procedure in step 312 employs subtraction image-based edge detection on the noise attenuated images, and computes the overall magnitude of the soft tissue edges, i.e., the edges of the motion correction field, in step 314 for the generation of a subtracted soft tissue image 316 with simultaneous corrections for large and small motion artifacts. Once the DL model 190 is optimized, the AI-based motion correction system 180 including the DL model 190 can be transferred to and/or employed on the imaging system 10 to provide the simultaneous large and small artifact correction.

Figure 7:
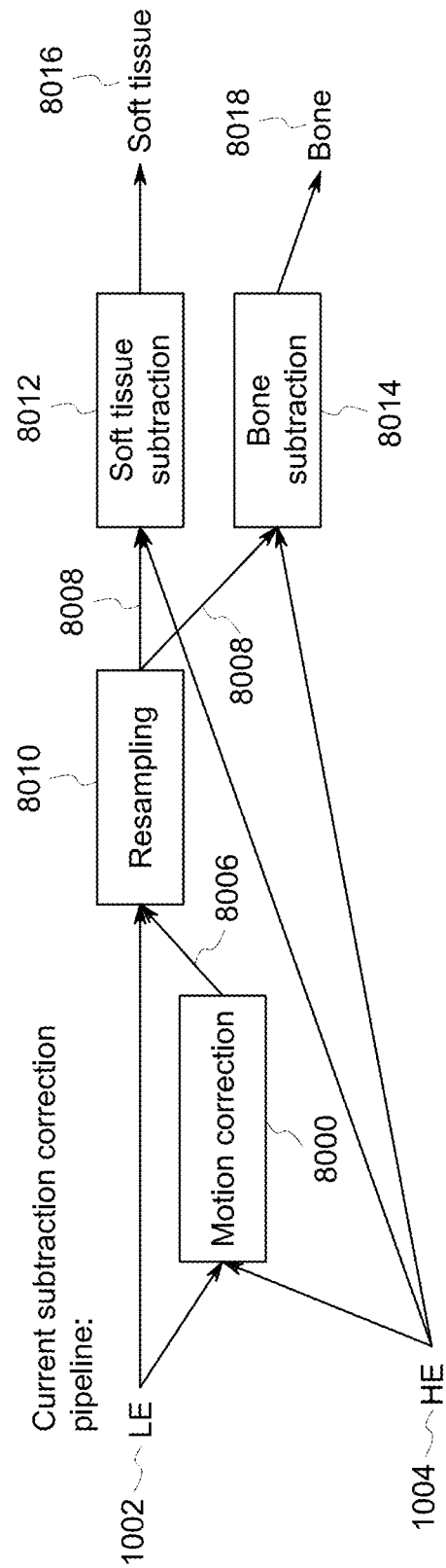
FIG. 7 is a schematic view of a prior art subtraction motion correction system employed on a dual energy imaging system.

Referring now to FIGS. 7-11, a prior art motion correction process is shown in FIG. 7 in which a single 2D motion correction 8000 is computed based on the low energy projection 1002 and high energy projection 1004 obtained by the dual energy imaging system 100 to provide a motion correction field 8006. The motion correction field 8006 is subsequently used to resample 1002 to produce a resample image 8008 that is subsequently processed through a soft tissue subtraction 8012 and a bone tissue subtraction 8014 to produce a motion corrected soft tissue image 8016 and a motion corrected bone tissue image 8018. The implementation of a single motion correction 8000 has limitations as it cannot compensate for all possible 3D motions of the subject. There are cases when different anatomical structures move in contradicting directions in a given point of the image, such as rib cage vs lung tissue. In such cases, using a common motion may not satisfy the motion correction need on soft and bone subtracted images at the same time. However, in a typical situation airways and lung tissue motion artifacts are less problematic on the soft tissue image, while quite visible on bone image.

Figure 8A:
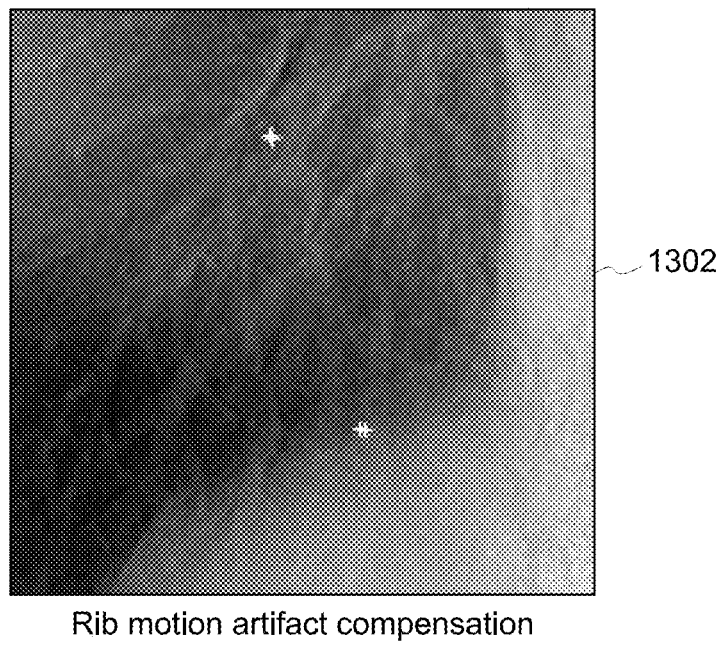
FIGS. 8A and 8B are illustrations of subtracted soft tissue images with soft and bone tissue artifact compensation.
Figure 8B:
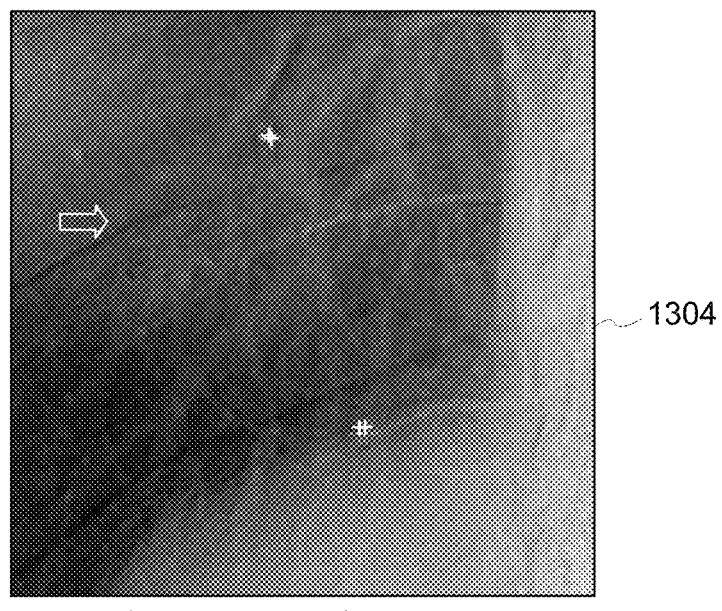
Figure 9A:
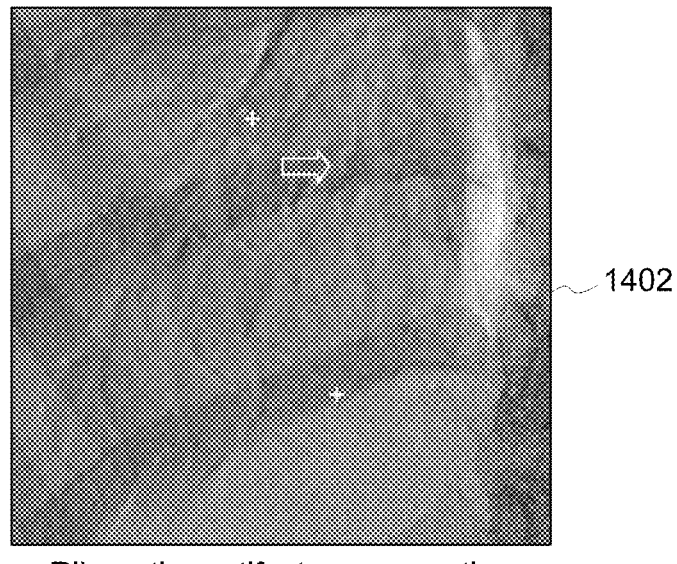
FIGS. 9A and 9B are illustrations of subtracted bone tissue images with soft and bone tissue artifact compensation.
Figure 9B:
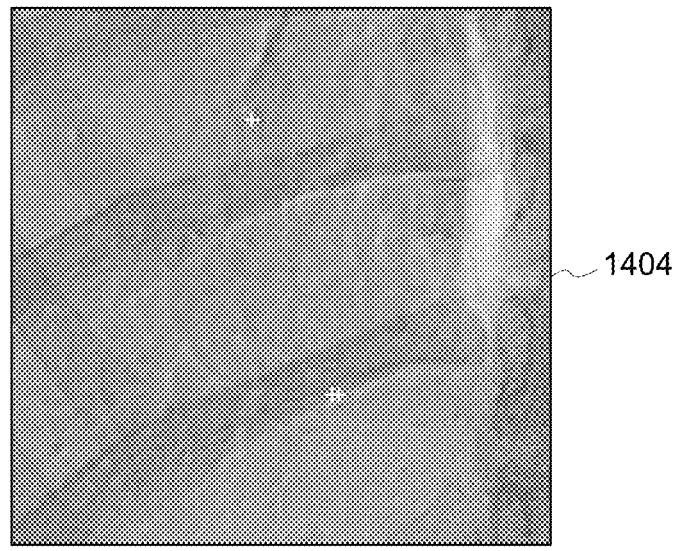

To accommodate for the differences in the different types of artifacts present in soft tissue images and bone images, according to another exemplary embodiment of the disclosure, the AI-based motion correction system 180 and/or DL model 190 can be configured to apply separate motion corrections for the generation of a soft tissue subtracted image and for the generation of a bone or dense tissue subtracted image. In FIGS. 8A and 9A, images 1302, 1402 represent bone motion artifact compensated images, and in FIGS. 8B and 9B, images 1304, 1404 represent soft tissue motion artifact compensated images.

Figure 10:
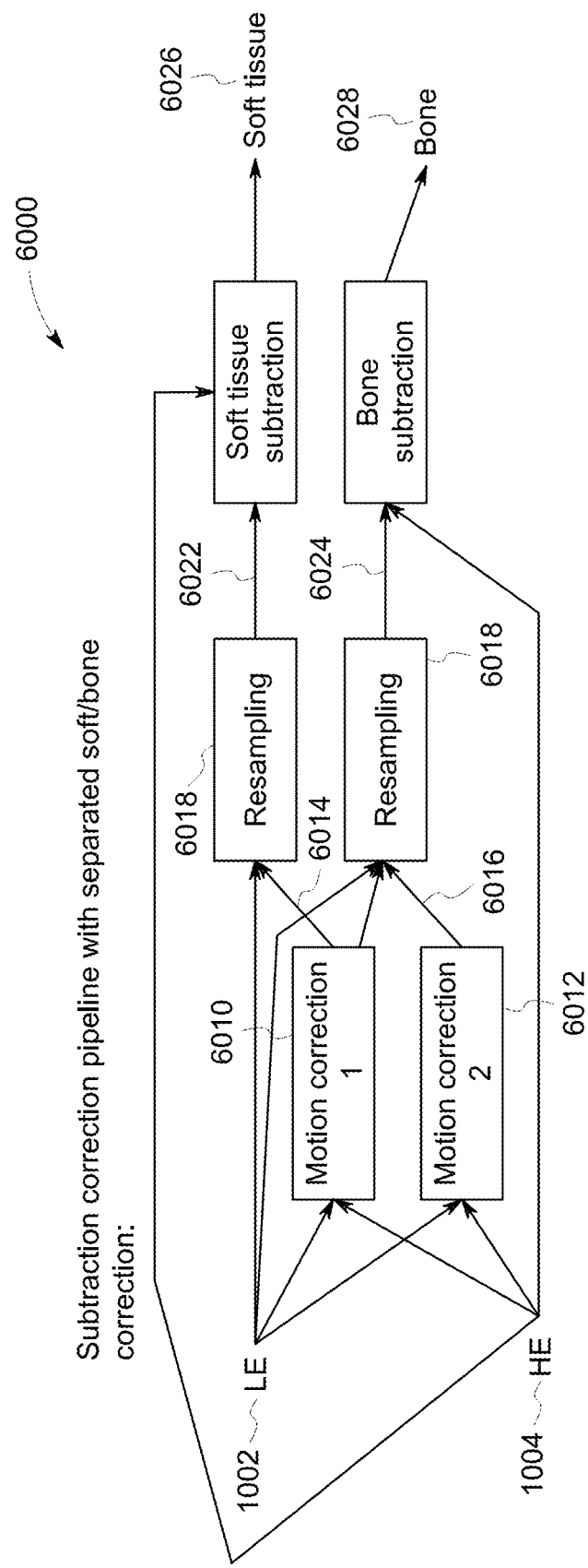
FIG. 10 is a schematic view of a subtraction motion correction system employed on a dual energy imaging system according to one exemplary embodiment of the disclosure.

Looking at FIG. 10, the AI-based motion correction system 180 and/or DL model 190 on the imaging system 100 separates the applied motion correction fields into soft tissue motion correction and bone tissue motion correction, such that the motion corrections can be separately tuned for the soft tissue and bone images according to the diagnostic quality needs. In the exemplary illustrated method 6000 of application of the AI-based motion correction system 180/DL model 190 on the imaging system 100, a low energy projection and/or image 1002 and a high energy projection and/or image 1004 obtained by the imaging system 100 are provided to the DL model 190. The DL model 190 proceeds to apply a first, or soft tissue motion correction 6010 and a second, or bone tissue motion correction 6012 to each of projections and/or images 1002, 1004 to form a first motion correction field 6014 and a second motion correction field 6016, where in an exemplary embodiment the first motion correction 6010 and the second motion correction 6012 are stored in the imaging system 100 memory 128 as a set of instructions for the AI-based motion correction system 180/DL model 190 to performed the motion corrections. The first and second motion correction fields 6014, 6016 then subsequently used by resampling processes 6018, 6020 to form a first resampled image 6022 and a second resampled image 6024. The first resampled image 6022 is run through a soft tissue subtraction process, with the high energy projection 1004 to form the subtracted soft tissue image 6026 and the second resampled image 6024 is run through a bone subtraction process with the high energy image 1004 to produce a bone subtracted image 6028. As each of the first motion correction 6010 and the second motion correction 6012 provide motion correction specific to the type of motion artifacts for the tissue type removed in the images output from the subtraction or decomposition processes, thereby providing significant improvement to the removal of these artifacts from the resulting subtracted images, i.e., improved removal of bone tissue motion artifacts from the soft tissue subtracted image 6026 and soft tissue motion artifacts from the bone subtracted image 6028.

Figure 11:
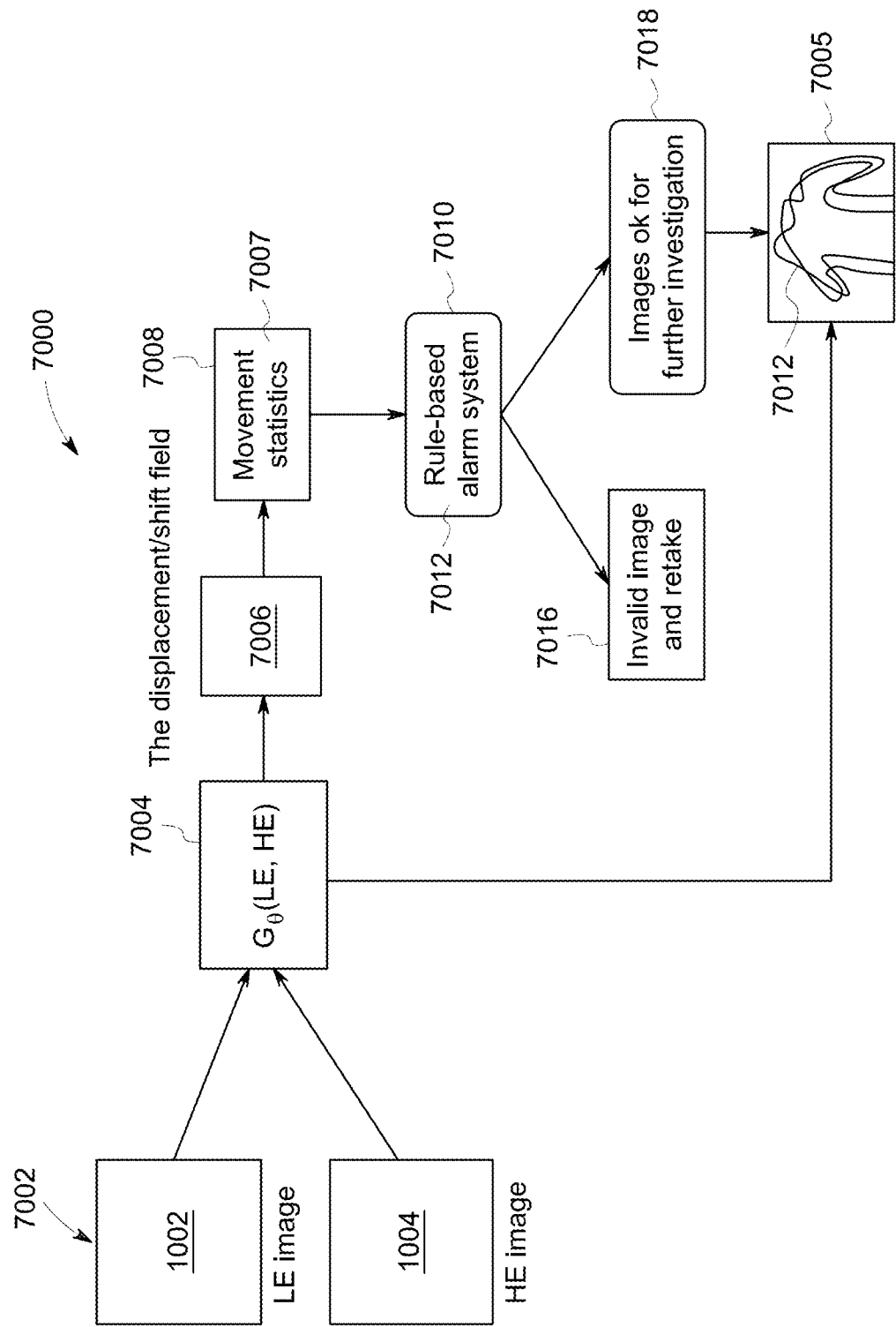
FIG. 11 is a schematic view of a motion alarm system for a dual energy imaging system according to one exemplary embodiment of the disclosure.

In addition to or separately from any one or more or the prior described exemplary embodiments of the AI-based motion correction system 180/DL model 190 on the imaging system 100, the AI-based motion correction system 180 can be configured to determine whether any motion occurring between the low energy image 1004 and the high energy image 1006 is of sufficient magnitude to warn the reader regarding the problematic diagnostic quality or indicate the retaking of the low energy image 1004 and the high energy image 1006. Referring now to FIG. 11, according to an exemplary embodiment of the disclosure, in the method of operation 7000 of the AI-based motion correction system 180 and/or the DL model 190 to determine the need for a warning, initially in step 7002 the low energy projection 1002 and the high energy projection 1004 are obtained by the imaging system 100. In subsequent step 7004 the low energy projection 1002 and high energy projection 1004 are registered with one another by the AI-based motion correction system 180/DL model 190 on the imaging system 100 for form aligned low and high energy images 7005. The AI-based motion correction system 180/DL model 190 can be trained to perform the registration process in any suitable manner, such as by the implementation of one or more of the training methods previously described regarding the organ segmentation and/or the noise attenuation in soft tissue edge detection, among others. In association or subsequent to the registration process, the AI-based motion correction system 180/DL model 190 in step 7006 predicts a registration or motion correction field between the low energy projection 1002 and the high energy projection 1004, to subsequently determine one or more movement statistics 7007 in step 7008 with regard to the aligned images. These movement statistics 7007 provide an indication of the magnitude of the movement that occurred between low energy projection and the high energy projection, and can include, for example, one or more of the mean movement with regard to the body of one or more of the whole body, the heart and/or lungs, as well as the percent of movement within the registration field, i.e., between the aligned low and high energy images, of the entire body, the heart and/or the lungs, among other suitable movement statistics. In step 7010, the AI-based motion correction system 180/DL model 190 compares the determined values of the movement statistics 7007 with a set of rules 7012 stored within the imaging system 10 and employed by the AI-based motion correction system 180/DL model 190. The rule set 7010 can be user-defined and/or modifiable, and includes a number of rules regarding various attributes of the registered/aligned low and high energy images, such as the mean movement statistics between the aligned low and high energy images of the body, or one or more organs, including the heart and lungs among others, and/or the percent of movement between the aligned low and high energy images of the body, or one or more organs, including the heart and/or lungs, among other potential rules. Alternatively, or in conjunction with the comparison of the movement statistics 7007 with the rule set 7010, the AI-based motion correction system 180/DL model 190 can provide a visual representation of the movement statistics on the aligned low and/or high energy images showing the magnitude of the movement detected. The visual representation can take any suitable form, such as an outline overlay 7014 of the position of one of the aligned low or high energy images on the other provided to the technician via the output 150.

After comparing the movement statistics 7007 to the rule set 7010, if one or more of the movement statistics violate or exceed the values provided by the rule set 7010, in step 7016 the imaging system 100 outputs a message to the technician, such as on the display 150, that the aligned images include an unacceptable level of movement between the low energy image and the high energy image and that a retake of the projections is suggested or required. Alternatively, if the movement statistics 7007 are within the parameters set by the rules 7010, in step 7018 the imaging system 100 can output a confirmatory message to the technician that the aligned images are within the parameters desired for acceptable LE and HE images and can be utilized for further investigative and diagnostic purposes. Further, even if the movement statistics 7007 fall within the parameters of the tule set 7010, the imaging system 100 can present the overlay with the LE and/or HE image to allow the technician to determine if a retake of the images is necessary based on user preference.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, each of the described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A method for improving motion correction in images of a subject obtained from a dual energy subtraction radiography x-ray system, the method comprising the steps of:
   a. providing an image processing system capable of processing image data comprising one or more high energy (HE) x-ray image(s) and one or more low energy (LE) x-ray image(s) of the subject, the image processing system comprising:
      i. a processing unit for processing the HE x-ray image data and the LE x-ray image data to form images; and
      ii. non-transitory memory operably connected to the processing unit and storing instructions for the operation of a motion correction system employed within the image processing system;
   b. providing a training dataset including a number of pairs of training HE x-ray images and training LE x-ray images of one or more objects;
   c. training the motion correction system to register one of the training HE x-ray image and the training LE x-ray image of each training dataset pair to the other of the training HE x-ray image and the training LE x-ray image of each training dataset pair by applying a first motion correction to the training x-ray image pair; and
   d. employing the motion correction system on a dual energy x-ray imaging system to apply the first motion correction to an actual HE image and an actual LE image obtained by the dual energy x-ray imaging system.

2. The method of claim 1, wherein the motion correction system is formed of a deep learning module, and wherein the step of training the motion correction system comprises training the deep learning module.

3. The method of claim 2, wherein the step of training the deep learning module comprises the steps of:
   a. computing areas of soft tissue within each pair of training HE x-ray images and training LE x-ray images with a soft tissue subtraction process;
   b. removing noise within the computed areas of soft tissue;
   c. computing a magnitude of edges within the computed areas of soft tissue; and
   d. altering one or more parameters of the deep learning module to minimize the magnitude of the edges of the computed areas of soft tissue.

4. The method of claim 1, wherein the step of training the motion correction system to register the training HE x-ray image to the training LE x-ray image comprises applying simulated anatomical movement to one of the training HE x-ray image or the training LE x-ray image.

5. The method of claim 4, wherein the step of applying simulated anatomical movement comprises the steps of:
   a. selecting an object of the anatomy within the training HE x-ray image and the training LE x-ray image that undergoes motion between the training HE x-ray image and the training LE x-ray image;
   b. generating a simulated anatomical movement for the object;
   c. applying the simulated anatomical movement to one of the training HE x-ray image or the training LE x-ray image; and
   d. registering the training HE x-ray image or the training LE x-ray image to which the simulated anatomical movement has been applied to the other of the training HE x-ray image or the training LE x-ray image.

6. The method of claim 5, wherein the step of applying the simulated anatomical movement comprises:
   a. generating an object-specific predicted anatomical movement for the object; and
   b. applying the object-specific predicted anatomical movement to the object in one of the training HE x-ray image or the training LE x-ray image.

7. The method of claim 1, further comprising the steps of:
   a. determining a measure of displacement of the object or a portion of the object between the HE x-ray image and LE x-ray image based on the motion corrections; and
   b. triggering an alarm if the determined measure of displacement exceeds a predetermined threshold.

8. A method for improving motion correction in images of a subject obtained from a dual energy subtraction radiography x-ray system, the method comprising the steps of:
   a. providing an x-ray system comprising:
      i. an x-ray source, and an x-ray detector alignable with the x-ray source;
      ii. an image processing system operably connected to the x-ray source and x-ray detector to operate the x-ray source to generate HE and LE x-ray image data, the image processing system including a processing unit for processing the HE and LE x-ray image data from the detector to form an actual HE image and an actual LE image from the image data;
      iii. non-transitory memory operably connected to the processing unit and storing instructions for the operation of a motion correction system;
      iv. a display operably connected to the image processing system for presenting the images to a user; and
      v. a user interface operably connected to the image processing system to enable user input to the image processing system,
   wherein the motion correction system is trained using a training dataset including a number of pairs of training HE x-ray images and training LE x-ray images of one or more objects to register one of the training HE x-ray image and the training LE x-ray image of each training dataset pair to the other of the training HE x-ray image and the training LE x-ray image of each training dataset pair by applying a first motion correction to the training x-ray image pair;
   b. operating the x-ray system to obtain the HE and LE x-ray image data;
   c. forming the actual HE x-ray image and the actual LE x-ray image; and
   d. performing a first subtraction process on the actual HE x-ray image and the actual LE x-ray image to form at least one of a soft tissue image and a bone tissue image after employing the motion correction system to apply the first motion correction to the actual HE x-ray image and the actual LE x-ray image.

9. The method of claim 8, further comprising the step of employing the motion correction system to apply a second motion correction to the actual HE x-ray image and the actual LE x-ray image, where the soft tissue image is provided by the first motion correction and the bone tissue image is provided by the second motion correction.

10. The method of claim 9, further comprising the step of performing a second subtraction process on the actual HE x-ray image and the actual LE x-ray image after employing the motion correction system to apply the second motion correction to bone tissue in the HE and LE x-ray images via the motion correction system.

11. The method of claim 9, wherein the motion correction system comprises a first deep learning module for applying the first motion correction and a second deep learning module for applying the second motion correction, wherein the step of employing the motion correction system to apply the first motion correction comprises employing the first deep learning module to apply the first motion correction, and wherein the step of employing the motion correction system to apply the second motion correction comprises employing the second deep learning module to apply the second motion correction.

12. An x-ray system comprising:
   a. an x-ray source, and an x-ray detector alignable with the x-ray source;
   b. an image processing system operably connected to the x-ray source and x-ray detector to operate the x-ray source to generate HE and LE x-ray image data, the image processing system including a processing unit for processing the HE and LE x-ray image data from the detector to form an actual HE image and an actual LE image from the image data;
   c. non-transitory memory operably connected to the processing unit and storing instructions for the operation of a motion correction system;
   d. a display operably connected to the image processing system for presenting the images to a user; and
   e. a user interface operably connected to the image processing system to enable user input to the image processing system;
   wherein the processing unit and non-transitory memory for the motion correction system is configured to obtain the actual HE x-ray image and the actual LE x-ray image of the subject and to register the actual HE x-ray image to the actual LE x-ray image by applying a first motion correction to the actual HE x-ray image and the actual LE x-ray image via the motion correction system, and
   wherein the processing unit and non-transitory memory storing instructions for the motion correction system is configured through a training procedure comprising the steps of:
      i. providing a computer including the motion correction system with a training dataset including a number of pairs of training HE x-ray images and training LE x-ray images of one or more objects; and
      ii. training the motion correction system to register one of the training HE x-ray image and the training LE x-ray image of each training dataset pair to the other of the training HE x-ray image and the training LE x-ray image of each training dataset pair by applying a first motion correction to the training x-ray image pair.

13. The x-ray system of claim 12, wherein the processing unit and non-transitory memory storing instructions for the motion correction system is configured to provide the first motion correction through a training procedure comprising the steps of:
   a. providing a computer including the motion correction system with a training dataset including a number of pairs of training HE x-ray images and training LE x-ray images of an object;
   b. computing areas of soft tissue of the object within the training HE and LE x-ray images of the training dataset via soft tissue subtraction;
   c. removing noise within the computed areas of soft tissue;
   d. computing a magnitude of edges within the computed areas of soft tissue; and
   e. altering one or more parameters of the deep learning module to minimize the magnitude of the edges of the computed areas of soft tissue.

14. The x-ray system of claim 12, wherein the processing unit and non-transitory memory storing instructions for the motion correction system is configured through a training procedure comprising the steps of:
   a. providing a computer including the motion correction system with a training dataset including a number of pairs of training HE x-ray images and training LE x-ray images of an object;
   b. generating a simulated anatomical movement for the object;
   c. applying the simulated anatomical movement to one of the training HE x-ray image or the training LE x-ray image; and
   d. registering the training HE x-ray image or the training LE x-ray image to which the simulated anatomical movement has been applied to the other of the training HE x-ray image or the training LE x-ray image.

15. The x-ray system of claim 12, wherein the processing unit and non-transitory memory for the motion correction system comprises a deep learning module.

16. The x-ray system of claim 15, wherein the deep learning module comprises:
   a. a first deep learning module configured to apply a first motion correction to the actual HE x-ray images and actual LE x-ray images; and
   b. a second deep learning module configured to apply a second motion correction to the actual HE x-ray images and actual LE x-ray images.

17. The x-ray system of claim 16, wherein the processing unit and non-transitory memory for the motion correction system is configured to perform a soft tissue subtraction on the actual HE x-ray images and actual LE x-ray images after application of the first motion correction to the HE x-ray images and LE x-ray images, and to perform a bone tissue subtraction on the actual HE x-ray images and actual LE x-ray images after application of the second motion correction to the actual HE x-ray images and actual LE x-ray images.

18. The x-ray system of claim 12, wherein the processing unit and non-transitory memory for the motion correction system is configured to determine a measure of displacement of the object or a portion of the object between the actual HE x-ray image and the actual LE x-ray image and to trigger an alarm if the measure of displacement exceeds a predetermined threshold.

19. A dual energy x-ray system comprising:
   a. an x-ray source, and an x-ray detector alignable with the x-ray source;
   b. an image processing system operably connected to the x-ray source and x-ray detector to generate x-ray image data, the image processing system including a processing unit for processing the x-ray image data from the detector;
   c. non-transitory memory operably connected to the processing unit and storing instructions for operation of a motion correction system;
   d. a display operably connected to the image processing system for presenting information to a user, and
   e. a user interface operably connected to the image processing system to enable user input to the image processing system;
   wherein the processing unit and non-transitory memory for the motion correction system is configured to apply a first motion correction to HE and LE x-ray images to facilitate the computation of soft tissue subtraction, and to apply a second motion correction to the HE and LE x-ray images to facilitate the computation of bone tissue subtraction, and
   wherein the processing unit and non-transitory memory storing instructions for the motion correction system is configured through a training procedure comprising the steps of:
      i. providing a computer including the motion correction system with a training dataset including a number of pairs of training HE x-ray images and training LE x-ray images of one or more objects; and
      ii. training the motion correction system to register one of the training HE x-ray image and the training LE x-ray image of each training dataset pair to the other of the training HE x-ray image and the training LE x-ray image of each training dataset pair by applying a first motion correction to the training x-ray image pair.

20. The dual energy x-ray system of claim 19, wherein the processing unit and non-transitory memory for the motion correction system is configured to determine a measure of displacement of the object or a portion of the object between the actual HE x-ray image and the actual LE x-ray image and to trigger an alarm if the measure of displacement exceeds a predetermined threshold.

* * * * *